(12) United States Patent
Bartuli et al.

(10) Patent No.: US 9,267,925 B2
(45) Date of Patent: Feb. 23, 2016

(54) POLE INTEGRITY METER AND METHOD OF DETERMINING POLE INTEGRITY

(75) Inventors: Alexej Bartuli, Riviera Beach, FL (US); Dmitrii Popov, St-Petersburg (RU); Alexandr Matyash, St-Petersburg (RU); Limanov Igor, Gatchina (RU); Belalami Salim, St-Petersburg (RU)

(73) Assignee: PoleXpert, LLC, Riviera Beach, FL (US)

(*) Notice: Subject to any disclaimer, the term of this patent is extended or adjusted under 35 U.S.C. 154(b) by 423 days.

(21) Appl. No.: 13/606,685

(22) Filed: Sep. 7, 2012

(65) Prior Publication Data

US 2014/0069192 A1 Mar. 13, 2014

(51) Int. Cl.
*G01N 29/12* (2006.01)
*G01N 29/22* (2006.01)

(52) U.S. Cl.
CPC ............ *G01N 29/12* (2013.01); *G01N 29/226* (2013.01); *G01N 2291/0238* (2013.01); *G01N 2291/02827* (2013.01)

(58) Field of Classification Search
USPC ......................................................... 73/579
See application file for complete search history.

(56) References Cited

U.S. PATENT DOCUMENTS

| | | | |
|---|---|---|---|
| 3,531,983 A * | 10/1970 | Heath et al. ...................... 73/584 |
| 4,329,882 A | 5/1982 | Kaup | |
| 4,350,044 A * | 9/1982 | Richardson et al. ............ 73/600 |
| 4,495,518 A | 1/1985 | Sanoian | |
| 4,702,111 A | 10/1987 | Holland | |
| 4,926,691 A * | 5/1990 | Franklin et al. ................. 73/579 |
| 5,105,453 A | 4/1992 | Hanrahan et al. | |
| 5,804,728 A | 9/1998 | Beall et al. | |
| 6,055,843 A * | 5/2000 | Schatz ......................... 73/12.01 |
| 6,347,551 B1 * | 2/2002 | Turpening et al. .............. 73/628 |
| 6,813,948 B1 * | 11/2004 | Rinn ............................... 73/584 |
| 6,823,736 B1 * | 11/2004 | Brock ................ G01N 29/0609 73/587 |
| 7,743,668 B2 | 6/2010 | Deuar | |
| 7,971,485 B2 * | 7/2011 | Greenough et al. ............. 73/602 |
| 2002/0148293 A1 * | 10/2002 | Little ..................... G01N 29/11 73/579 |
| 2003/0131674 A1 * | 7/2003 | Foley et al. ..................... 73/866 |
| 2005/0011249 A1 * | 1/2005 | Mahaffey et al. ............ 73/12.01 |
| 2008/0255806 A1 * | 10/2008 | Sambuelli et al. ............. 702/183 |

FOREIGN PATENT DOCUMENTS

WO WO-2010/046844 A2 * 4/2010 ............. G01N 29/04

OTHER PUBLICATIONS

Vonaq, CXI-PT5000, Innovative pole testing technology, product brouchure, 2010, Vonaq Ltd. www.vonaq.com.*

* cited by examiner

*Primary Examiner* — Andre Allen
(74) *Attorney, Agent, or Firm* — McHale & Slavin P.A.

(57) ABSTRACT

The present invention provides a non-intrusive method and device for determining the integrity of a support structure, such as a wooden utility pole. The determination of the structure's integrity is based on the relationship between the structures natural frequency and one or more mechanical and geometrical characteristics. The method includes the steps of generating an acoustic signal, converting the signal into digital signal that can be analyzed, and calculating the structure's strength and mechanical characteristics of the pole over time.

13 Claims, 6 Drawing Sheets

POLE INTEGRITY METER AND METHOD OF DETERMINING POLE INTEGRITY

FIELD OF THE INVENTION

The present invention is related to evaluating support structure members, and more particularly, to a device and method for using acoustic signaling to determine the integrity of one or more support structures, such as wooden or cement pole structures, utilizing non-destructive and non-invasive techniques.

BACKGROUND OF THE INVENTION

Support structures, such as wooden poles, are common features along municipal landscapes. These structures are primarily used as support structures for power lines and other utility services, such as telephone cables or fiber optics, and equipment, such as transformers and street lights. While some cities have recently begun installing power lines or cables underground, a significant number of wooden poles remain as the primary support structure. Moreover, burying cables underground can be cost prohibitive. Given the large number of such structures in existence, the ability to preserve the wooden poles and characterize the integrity of the structures over time is paramount, as replacing the poles is labor intensive and can involve considerable costs. In addition, since many of the wooden poles are located in highly populated areas, pole replacement can be disruptive, causing road closures or possible disruption of services and/or slow-down of pedestrian traffic near the affected area.

Preservation techniques for preventing wooden materials from deterioration are used as a primary means for extending their useful life. Most preservation techniques fall into two main classes: 1) oil-borne preservatives, such as creosote, pentachlorophenol in petroleum, and copper napthenate; and 2) water-borne preservatives, such as arsenates of copper, including ammoniacal copper zinc arsenate and chromated copper arsenate. These techniques, however, have not been able to provide fail safe preservation means, particularly for utility poles that are routinely exposed to multiple risk factors. Accordingly, a need for continued monitoring of the structural integrity of these structures is needed.

Numerous factors are associated with the deterioration of utility poles. Because the utility poles support vertical, longitudinal, and transverse loads caused by wire tension, weight of coupled objects, and wind, the pole's structural characteristics must be monitored over their lifetime to obtain maximum useful life. In order to successfully monitor the structure over a time period, the ability to determine the overall integrity is paramount. Continuous monitoring provides pole owners the capability of preventing, or at least minimizing, unexpected load failure, thereby reducing the risk of pole collapse, human injury, and property damage. Knowing the pole integrity allows pole owners a reliable mechanism to determine if the structure should be repaired or replaced. Knowing the structural integrity of the poles further allows pole owners the ability to predict replacement times, thereby providing better budgeting analysis and accommodations. Characterizing the structural integrity of each pole further allows the owner the capability to remove excess load which could cause immediate failure or deterioration.

While the type of wooden structures used by municipalities may differ, i.e. western red cedar, Douglas fir, other pines, deterioration is common to all types of wooden structures. Most wooden structures are susceptible to various environmental attacks, such as the gradual deterioration resulting from internal damage caused by insect attack. Termites, ants, and wood borers damage the internal composition of the wood structures which is difficult to accurately and properly access through external visualization techniques. The damage caused by the bio-attack often results in a relatively slow decay process, leaving the pole subject to failure at unpredictable times. Wood destroying fungi are another environmental hazard that results in weakening of the integrity of the wood structures. As mentioned previously, such wood structures can be treated to minimize the damage caused by such organisms. However, the chemical preservation procedures are not fail safe, and a mechanism for monitoring the structure's structural integrity and level of damage, if any, while undergoing treatment is needed. In addition, soil can affect the strength of the pole. For example, if the soil contains acid components, the acid destroys timber fibers and leads to the reduction of pole strength at a faster rate than soils that are less acidic. The presence of big cracks, knots, or moisture can also result in the reduction of pole strength. Even if a pole has no defects, the starting strength may be less than the statistical maxim. The present invention provides a reliable and reproducible system to determine the real, starting strength of the pole. For poles not made of wood fibers, other factors may be important. For concrete poles, the corrosion of reinforcement can result in reduction in pole strength.

Environmental conditions, such as extreme heat, cold, moisture, or lack of rainfall can result in accelerated damage as a result of the environmental conditions, or through increase in organism attack. While certain areas may result in faster decay times, a device and method which can determine structural integrity is needed for any structure that is exposed to the external environment. Finally, wooden structure decay can also result from man-made activities. Typically, chemical preservation treatment includes boring and injection of the chemicals into the structure's internal environment. The boring process, any cuts and/or injection sites can form a focus point for damage and decay.

Various inspection and maintenance programs are performed in order to identify and remove damaged wooden structures. Many programs utilize visual inspection as a primary means for determining the integrity of the wooden structures. Since visual assessment requires individuals to visually inspect each structure, this type of analysis is time consuming and labor intensive as the individual must inspect all parts of the structure's external surface and note any indications of possible damage. Visual inspection offers limited useful information in the assessment analysis and can be problematic because the measurements are subjective, deterioration over a period cannot be properly quantified, nor can the underground or internal aspects of the wooden structure be properly accessed.

Other detection methods are known in the art. For example, use of sound is a common mechanism for determining decay in wood structures. Sound based procedures include the use of an instrument which is placed around the periphery of the structure, at positions ranging from the ground level to the top of structure. The characteristics of the sound generated at each strike are evaluated in order to determine the deterioration. This method however, is subjective and the exact level of deterioration can not be properly assessed. If an area is suspected of possible deterioration, the pole is cored to obtain a sample for further evaluation. However, coring a sample from the wood pole allows oxygen, water, and fungi access to the internal environment. U.S. Pat. No. 4,329,882 describes a kit having tools for obtaining a core sample of an underground portion of a wood structure without the need for removing any ground material. Several other methods and/or devices for determining the pole integrity include U.S. Pat. No. 4,495, 518, U.S. Pat. No. 4,702,111, U.S. Pat. No. 5,105,453, U.S. Pat. No. 5,804,728, U.S. Pat. No. 7,743,668, and U.S. Patent Application Publication No. 2003/0131674.

Most of the existing methods range from simple sounding testing using a regular hammer to sophisticated techniques and devices capable of visualizing the inner timber structure. However, these testing methods provide for detecting defects only in a specific cross-section or at accessible areas. Devices using such methods can be considered as flaw detectors and fail to properly and comprehensively estimate the actual strength of a wooden pole entirely. While the most accurate method of bending strength determination is to apply a mechanical load to the pole until the pole reaches its breaking point, such approach is destructive and not applicable for in-service poles.

Therefore, what is needed in the art is an improved method and device which allows inspectors to determine the integrity of the structure, the strength of the structure, and the amount of load that can be applied to the structure in its current state which does not result in failure or further damage.

SUMMARY OF THE INVENTION

The present invention provides a non-intrusive method and device for determining the integrity of a support structure, such as a wooden utility pole, which includes, but is not limited to a determination of changes in geometric structure parameters, bending strength, conditions of embodiment and anchoring of the pole within the soil, pole capacity and stability. Support structures such as wooden utility poles have played a vital role in establishing the electrical system as electrical transmission and distribution lines, as well as cable and fiber optic lines, deliver power and other services to large cities, small towns, and rural outposts. With an estimated 130 million wood poles currently in service, and millions of new poles being introduced into the electrical system, a noninvasive method and device for determining the load capability of a support structure which minimizes the risk associated with unexpected load failure is desired. The present invention will allow inspection of numerous support structures in order to characterize the internal deterioration determining parameters of the structures. By determining these internal characteristics, the integrity of the pole can be determined, assessed, and monitored. The amount of weight the structures can bear without resulting in failure can be used to prevent unexpected failure and help extend the life of the existing structures. The method and device for determining the load capability of one or more utility poles in accordance with the instant invention, therefore, provides cities, municipalities, and rural areas with a noninvasive means for reducing the costs associated with maintaining and replacing the poles.

The device and testing method developed in accordance with the present invention allows for a relatively quick and easy assessment of the entire pole, from tip to about 35-50 cm below ground line, and estimation of the pole's remaining strength. The device and method in accordance with the present invention uses dual module determinations to estimate the pole's actual stratus, i.e. the residual/remaining resource/strength, and its residual lifetime. Assessment of the pole structure utilizes the pole's characteristics or parameters, such as its height, diameter, taper, wood species, and year of installation. These characteristics are input into and saved on a detection device memory. Based on these characteristics, a mathematical model of the pole with maximal timber strength is generated. This mathematical model represents the pole's maximal strength capacity, i.e. the amount of load it will carry without failure or breaking. An acoustic model is also determined by measuring the pole's acoustic response. The response is captured and its signal is processed and analyzed. Using the results of the pole signal analysis, and based on the pole's geometrical characteristics, a real/actual model of the pole will be generated. The second real/actual model represents the pole as it is. By comparing the pole's two models, an estimate of its actual strength status (residual/remaining resource/strength) and its residual lifetime is determined.

An illustrative example of the non-invasive method of determining the strength of a structure includes the steps of: 1) providing a testing device which is adapted to capture, analyze, and store data, the device having at least one sensor for capturing a signal; 2) inputting one or more strength determining characteristics of the structure into the device; 3) applying the sensor to the structure to be tested; 4) creating a vibrational frequency signal within the structure; 5) measuring the frequency signal with the device sensor; 6) analyzing the frequency signal; 7) providing data output. The data output is preferably a numerical determination of the strength of the structure wherein the determination is used to indicate the amount of weight the structure will hold without resulting in load failure, buckling or other damage.

Accordingly, it is an objective of the instant invention to teach a device and method for determining the integrity of a support structure.

It is a further objective of the instant invention to teach a noninvasive method for determining the integrity of a support structure.

It is yet another objective of the instant invention to teach a noninvasive method for determining the integrity of a wooden structure.

It is a still further objective of the instant invention to teach a noninvasive method for determining the integrity of a utility pole.

It is a further objective of the instant invention to teach a device and method for determining the load capability of a support structure.

It is yet another objective of the instant invention to teach a noninvasive method for determining the load capability of a support structure.

It is a still further objective of the instant invention to teach a noninvasive method for determining the load capability of a utility pole.

It is a further objective of the instant invention to teach a noninvasive method for determining the load capability of a support structure which minimizes the risk associated with unexpected load failure of the support structures.

It is yet another objective of the instant invention to teach a noninvasive method for determining the load capability of one or more utility poles which reduces the costs associated with maintaining and replacing the poles.

It is a still further objective of the invention to teach a noninvasive device and method for determining the load capability of a support structure which compares the structure's natural frequencies to the mechanical or geometrical parameters to determine the load capability.

It is a further objective of the instant invention to teach a device having one or more software programs and/or algorithms for determining the load capability of a support structure which compares the structure's natural frequencies to the mechanical or geometrical parameters to determine the load capability.

It is a further objective of the instant invention to teach a device having one or more software programs and/or algorithms which uses acoustic and mathematical models to determine a pole's load capability or residual resource.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
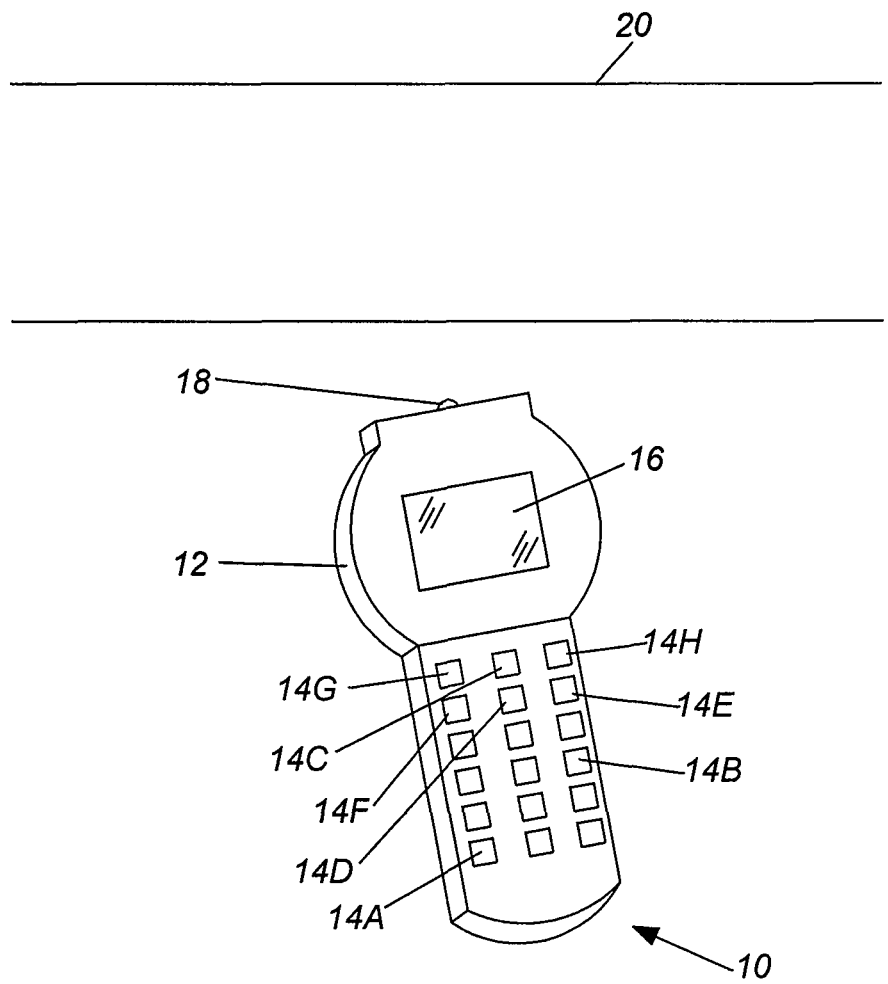
FIG. 1 is a perspective view of an illustrative example of a pole integrity determining device in accordance with the instant invention.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIG. 1, a pole integrity determining device 10 is shown. The device 10 contains an outer casing 12 which encloses the internal components of the device, including a power source such as a battery, a processor, a data storage device, signal converter devices, and the internal circuitry for performing its intended functions. The external components of the device include one or more command buttons, referred to generally as 14 and a data display unit 16. The command devices could be for example, a power on/off button 14A, buttons that allow the user to input numbers or letters 14B, arrow buttons 14C-14F, or other command buttons 14G-14H that allow the user to navigate the software system utilized with the device and visibly displayed on the data display unit 16. The digital display unit 16 is preferably one or more LCD screens, but may be any other display-type unit known to one of skill in the art.

Alternatively, the device 10 may contain one or more capacitance-based, or touch screen technology to allow the user to navigate the device through the use of on screen commands or manipulation. The pole integrity determining device 10 further contains one or more detecting elements designed to detect a specific signal or frequency. Preferably, the detecting element is a sonic or seismic sensor 18. The pole integrity determining device 10 is preferably a hand-held device which is sized and shaped to be carried within a pocket or holder.

Figure 2:
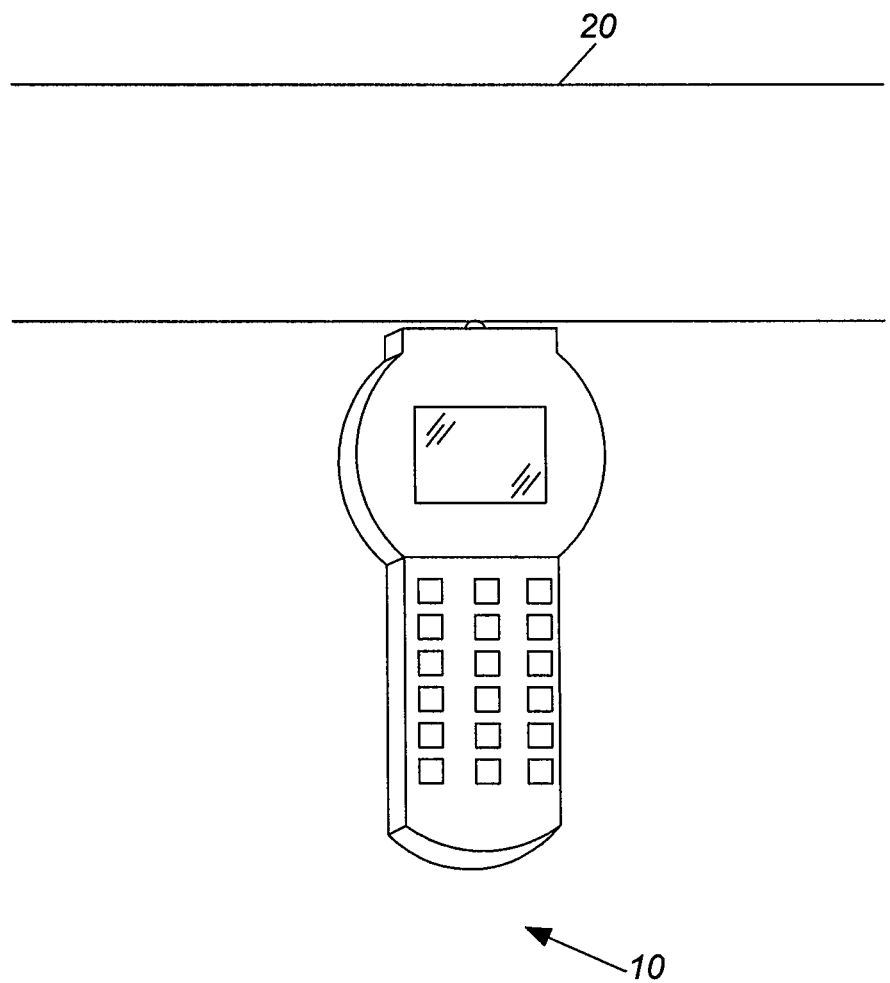
FIG. 2 is a perspective view of the pole integrity determining device illustrated in FIG. 1 shown contacting the pole structure.

Referring to FIGS. 1 and 2, a pole structure, illustrated herein as a wooden pole structure 20, is shown. However, the device can be used to determine the structural integrity of other structures, including cement structures, as the description of the wooden structure used throughout the description is not intended to be limiting. Referring to FIG. 2, the wooden pole integrity determining device 10 contacts the wooden pole 20 in order to measure any sound waves or seismic activity. Preferably, the sensor is capable of detecting any signal without the need for puncturing the outer surface of the wooden utility pole 20. In this manner, the pole integrity determining device 10 is non-intrusive and does not contribute to deterioration by creating areas which expose the structure to oxygen, water, and possible fungal attack.

The pole integrity determining device 10 is adapted to measure the vibrations of the pole structure 20 and transduce the vibration frequency into an electrical signal. The software program is designed to convert the signal into a value which is used to either determine the strength of the structure or determine other characteristics which can be used to determine the strength of the structure. Once the pole 20 strength is determined, the amount of load that the structure can bear is determined. According to the values determined, the user can then make a decision as to whether or not the pole 20 needs immediate replacement, or provide an estimated time as to when such replacement may need to occur.

Additionally, since the strength of the pole has been determined, the user can further ascertain the amount of load that can be placed onto the pole 20 which does not result in the critical load value. Should the value determined indicate that the structure cannot maintain the current load value, the owners of the pole can take the necessary next steps, such as replacing the entire structure or, if possible, reducing the amount of load currently applied to the pole 20. Since the level of deterioration or decay can affect the strength of the pole, the device 10 can be used to determine levels of decay as well as be the means of calculating or using one or more pole characteristics.

Figure 3:
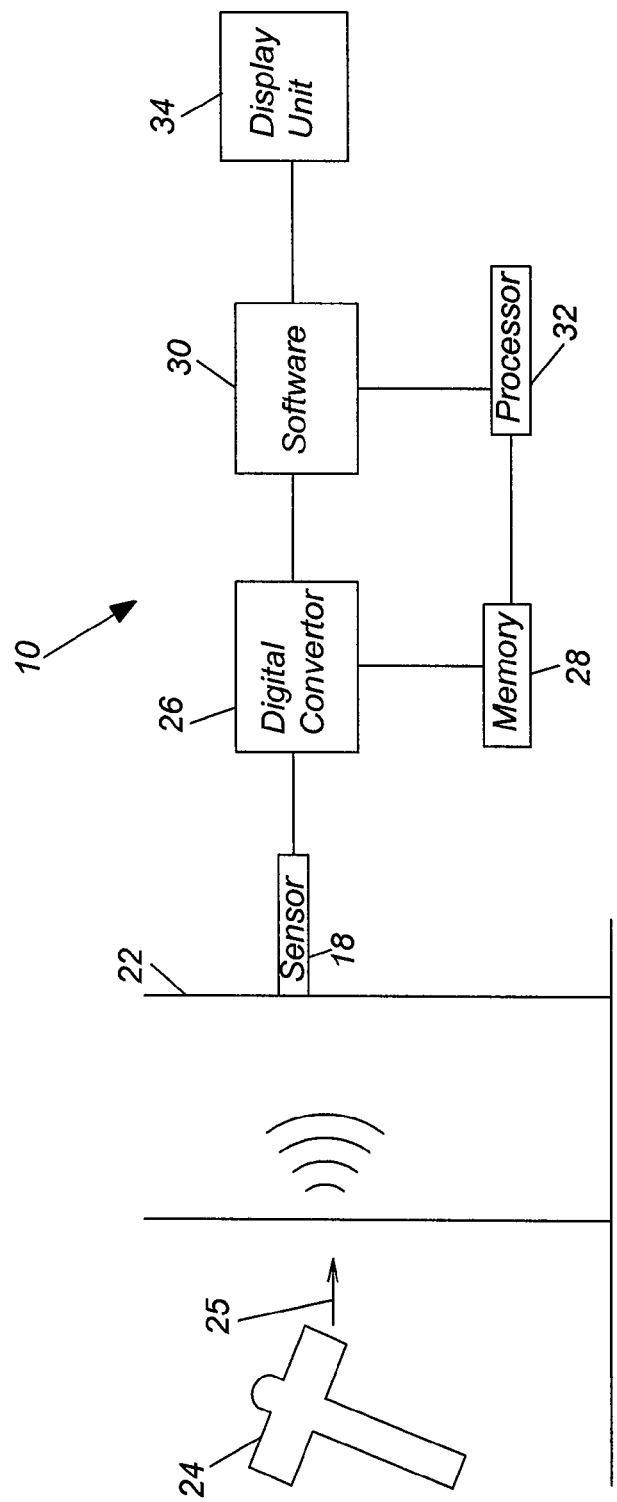
FIG. 3 is a schematic block diagram illustrating the internal aspects of the device illustrated in FIGS. 1 and 2.
Figure 4:
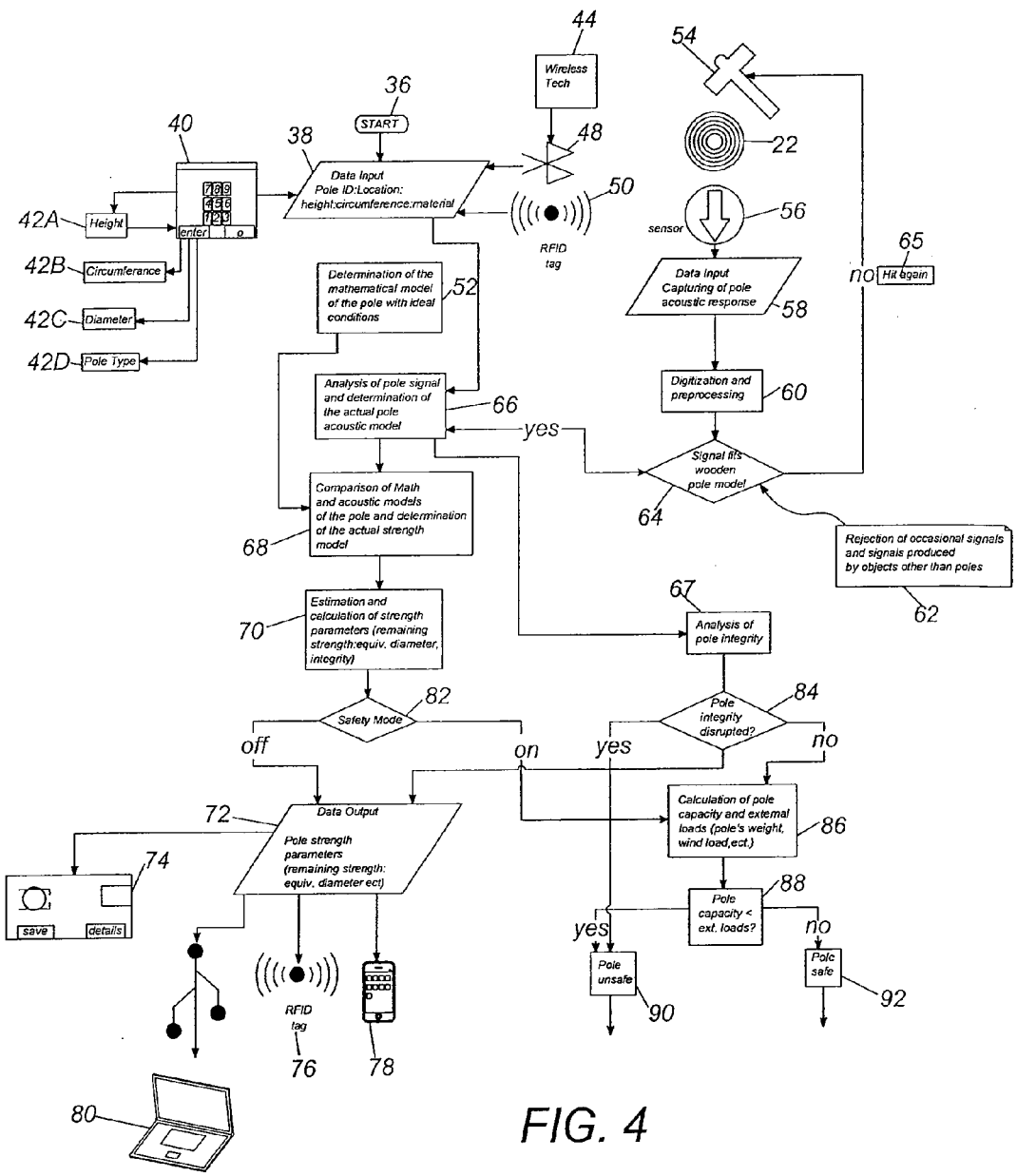
FIG. 4 is a flow chart describing an illustrative embodiment of the method of determining the strength of a structure in accordance with the instant invention.

The method of the preferred embodiment of the instant invention is implemented using the pole integrity determining device 10 as illustrated in FIGS. 1 and 2. The method in accordance with the instant invention is herein described as determining the integrity and strength of a wooden utility pole. However, the device and method in accordance with the instant invention can be used with other wooden structures as well as structures not made of wood. Referring to FIGS. 3 and 4, a vibrational frequency is generated by striking (see arrow 25) the wooden utility pole 22 with a striking device, illustrated herein as a mallet 24, see FIG. 3. The pole vibration generated by the mallet strike is sensed by the seismic sensor 18 which converts the acoustic signal into a signal which can be stored and used by a software program in order to determine the utility pole's strength.

Preferably, the acoustic signal is converted into an analog electrical signal and transformed into a digital signal using a digital converter 26. The digital signal is stored into a memory device 28, such as but not limited to memory modules used in personal computers. Data stored in the memory device 28 or converted through digital converter 26 can be used to create the necessary information through use of an analysis module, such as software programming 30 run by a processor 32, such as a CPU or microprocessor. All the data created by the software programming 30 can be displayed to the end user thorough the display module 34.

The method of determining the utility pole strength in accordance with the instant invention is based on the relationship between the utility pole's natural structure frequencies, which is determined by the frequency generated by the mallet strike, and the pole's mechanical and geometrical characteristics, including but not limited to elastic modulus, the density of the structure, and the cross-section area. Determining one or more of the utility pole's mechanical and geometrical characteristics allows for a determination of the pole's current overall strength as the mechanical and geometrical parameters reflect the presence of any decay, such as rotting, cracks, or presence of fungal infection, within the internal environment of the utility pole.

Understanding and quantifying the amount of decay within the structure provides an ability to determine the actual strength of the structure. The relationship between the utility pole's natural frequency and the mechanical and geometrical characteristics is described generally using mathematical equations, such as by Equation A:

$$f_{(i)} = \frac{1}{2\pi d^2} \cdot k_i^2 \cdot \sqrt{\frac{J \cdot E}{S \cdot \rho}},$$

where l is defined as the pole's or structure's length; S is defined as the cross-sectional area of the pole or structure; J is defined as the cross-sectional moment of inertia; $K_i$ is defined as the coefficient characterizing the ordinal number and location of a particular natural frequency; E is defined as the modulus of elasticity; and $\rho$ is defined as the density of the pole or particular structure, which in the instant illustration is the wood density. In addition to the above mentioned equation, the relationship between the value at which the pole fails, or its critical load value, and the mechanical and geometrical characteristics is described generally by Equation B:

$$F = \frac{\pi^2 E J}{2 l^2}$$

where l is defined by the utility pole's length; J is defined by the cross-sectional moment of inertia; and E is defined by the modulus of elasticity. The system in accordance with the present invention provides for measuring the strength of a pole using an acoustic model as well as a mathematical model. By measuring and/or inputting the values to one or more of the parameters in Equation A, and/or Equation B, or other equations independently or based on Equation A or B, a value of the pole's strength is determined.

The Mathematical Model. An installed wooden pole is considered a cantilever beam with one end anchored to the ground and made of anisotropic material (timber). The strength of such structure can be characterized by the actual bending stress of the pole which in turn depends on several conditions and factors, such as but not limited to 1) the presence of any internal or external decays (rotting, cracks etc); 2) embodiment and quality of the anchoring to the ground; 3) quantity of moisture absorbed by timber, i.e. the more moisture in the timber, the lower the bending strength; and 4) static and dynamic loads (the tension of wires, attached equipment, wind load, the pole's weight etc). The remaining bending strength (in %) of a wooden pole can be described by the following Equations.

$$R(\%) = \frac{M'}{M_{max}} [\%] \quad \text{Equation (1)}$$

Where:
R=the remaining strength [%];
M'=the maximum actual bending moment of the pole taking into account the actual status and conditions of the pole (decays, embodiment, moisture, static loads) [kgf*cm];
$M_{max}$=the maximum bending moment of a pole with same dimensions (height and diameter), made of healthy timber, with maximum bending stress (495 kgf/cm$^2$), with moisture content of 25-30% and without external loads [kgf*cm].

Equation 2 is as follows:

$$M' = (F' - \Sigma F_{st}) * H_{[kgf*cm]}$$

Where:
H=the height of the pole [cm].
F'=the maximum horizontal breaking load can be applied to the pole's tip taking into account the presence of any decays, moisture content and the conditions of the embodiment [kgf];
$\Sigma F_{st}$=the sum of statistic loads (pole's weight, static tension of wires, attached equipment etc.) applied to the pole's tip [kgf].

Equation (3) is as follows:

$$M_{max} = 0.2 d^3 * 495_{[kgf*cm]}$$

Where:
d=the diameter of cross-section at 35 cm below ground level [cm];
495 kgf/cm$^2$=the maximum bending stress for pine timber.

The Acoustic Model: The natural frequency depends only on the mechanical, physical and geometrical properties of the pole (presence of decays, conditions of the embodiment, static loads, etc). The correspondence between a natural frequency of a cantilever beam and the beam properties can be shown by the following equations.

$$f_i = F_i * \sqrt{\frac{E}{\rho}} [Hz] \quad \text{Equation (4)}$$

Where:
$f_i$=the value of natural frequency [Hz];
E=the elasticity modulus [kgf/cm$^2$];
$\rho$=the density of timber [kg/cm$^3$];
$F_i$=the coefficient which depends on the shape of the pole (height, cross-section diameter and pole taper) [1/cm].

$$\rho = \frac{m * 4}{H * D^2} [kg/cm^3] \quad \text{Equation (5)}$$

Where:
m=the total weight of the pole [kg];
D=the pole's average diameter (taking into account the taper of the pole) [cm];
H=the Height of the pole [cm].

$$F_i = k_i * \frac{D}{H^2} [1/cm] \quad \text{Equation (6)}$$

Where:

$K_i$=the coefficient which depends on the type and number of the natural frequency;

D=the pole's average diameter (taking into account the taper of the pole) [cm];

H=the height of the pole [cm].

Correspondence between sonic velocity and timber properties can be represented by Equation (7) as follows:

$$C = \sqrt{\frac{E}{\rho}} [cm/sec]$$

Where C=the sonic velocity [cm/sec].

By generating a mechanical pulse, i.e. using a hammer or a mallet, in the pole, an acoustic response (vibration and production of the pole's natural frequencies) is generated. The acoustic response does not depend on the power of the impact. The testing technique used in the present invention (analysis of natural frequencies) is based on the measurement and analysis of the natural frequencies of an installed pole. The presence of any decay (rotting, deterioration, cracks etc) reduces the mechanical properties of the pole and lead to the reduction of the values of its strength and natural frequencies. Thus, by measuring and analyzing the natural frequencies of the pole, the mechanical properties of the timber (density and elasticity) and estimation of the influence of any decay on the properties of the pole (coefficient Fi) can be determined.

In use, the process begins by identifying one or more utility pole structures 22 which need to be evaluated, see step 36, FIG. 4. Once the utility pole structures 22 have been identified, the inspector inputs data, step 38, into the pole integrity determining device 10 illustrated in FIG. 1, see step 40 and further described in FIG. 2. The data input into the device includes one or more pole characteristics which are used in determining the final data output, i.e. the pole strength, and includes, but is not limited to, one or more pole parameters such as an identification number unique to the individual utility pole, the location of the utility pole, the height (distance between the ground line and the pole's tip) of the utility pole, the circumference/diameter of the utility pole (measured at several heights or levels, such as at 0, 50 cm, 100 cm, 150 cm and 200 cm from ground level), and the type of material or species of the wood, see for example 42A-42D. While such characteristics may be directly input into the device 10, other data input mechanisms can be used, such as the use of wireless technology, such as Bluetooth technology 48, or RFID technology, using RFID tags 50. While most utility poles are made of some type of wood, the method of determining a structure's strength in accordance with the instant invention is not limited to determining wooden pole structures.

Accordingly, should the structure be identified as made of a material other than wood, such as concrete, the user may be instructed to input other types of data that relates specifically to that material through one or more subprograms designed to identify the pole type. Once the pole type has been determined, its mathematical model is determined, see step 52. The mathematical model takes into account the one or more utility pole parameters input in step 38 to determine a natural frequency.

With the pole integrity determining device 10 in contact with the utility pole 20 as shown in FIG. 3, the user creates a seismic moment by striking the utility pole 20 with a mallet, see step 54. The mallet strike in step 54 generates an acoustic signal, see FIG. 5A or 6A for illustrative example, which is detected by acoustic sensor, see step 56. The acoustic signal detected by the sensor is analyzed by an analysis module by receiving the response, or acoustic signal, from the strike and transducing that acoustic signal into a usable signal that can be manipulated by filtering out non-essential noise or signal, rejection of signals produced by other objects, and a determination if the signal fits the pole model, steps 58, 60, 62, and 64. Due to the specific structure of the wood fibers, the anisotropy of timber, and equipment attached to the pole, the analysis may be skewed. Accordingly, noise filtration methods may be employed. The device or system may therefore include mathematical algorithms of noise filtering and signal processing to simplify the acoustic signal of the pole and to make it readable and applicable for further analysis. Other noise filtering techniques known to one of skill in the art, such as the Fourier Transformation (FT), may be employed. The acoustic signal generated from the pole vibration is transformed into the digital signal, which is then stored and used in the analysis mode.

Figure 5A:
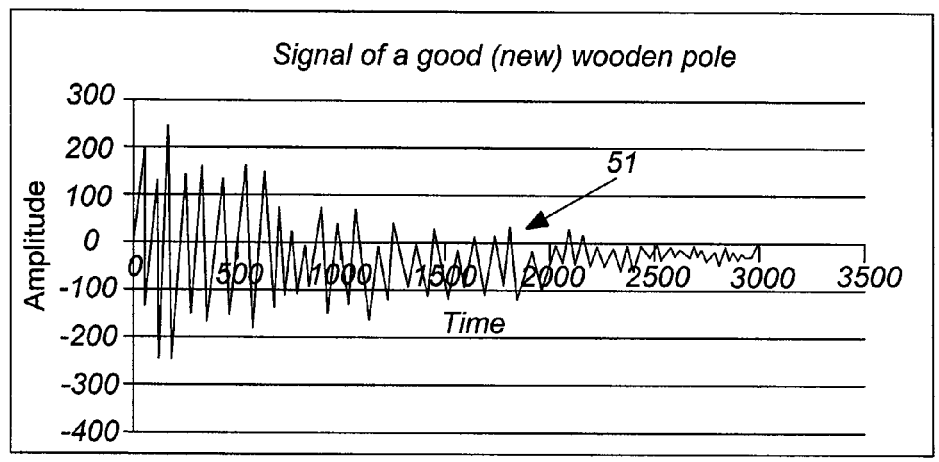
FIG. 5A is an illustrative example of an acoustic signal pattern generated by a wooden pole free of defects.
Figure 6A:
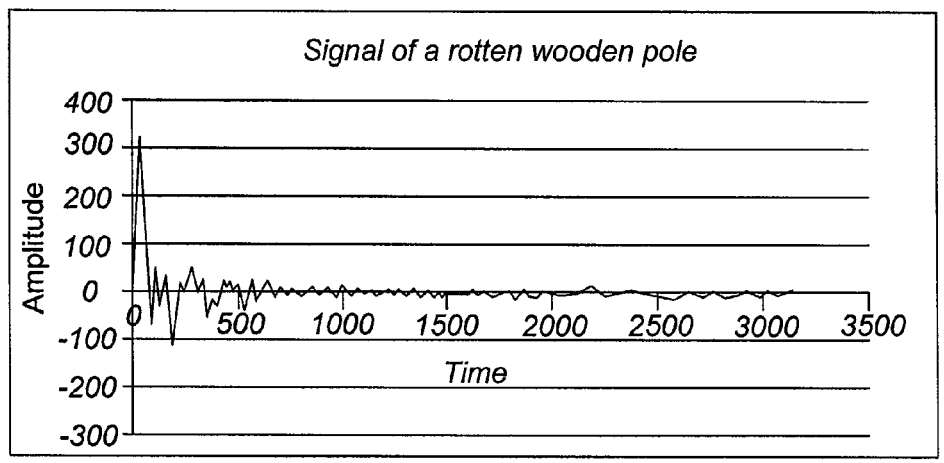
FIG. 6A is an illustrative example of an acoustic signal pattern for a rotting pole of the same fiber type as the pole used in FIG. 5A.

A preliminary analysis of the signal is used to determine if the signal contains the basic features of the utility pole. The acoustic module determined is combined with the mathematical model to provide a determination of pole strength and/or the amount of load that it can hold without failure. The acoustic model includes obtaining an acoustic pattern of the pole to be tested. FIG. 5A is an illustrative example of an acoustic signal pattern 51 generated by a new, healthy, i.e. free of defects, wooden pole. FIG. 6A is an acoustic signal pattern 53 for a rotting tree of the same fiber type. To determine the acoustic model, the signal pattern generated by the pole to be tested may be compared to other patterns stored in a library. The library, which is preferably an electronic database, contains known frequency patterns for all types of materials, such as the type of wood fiber that makes up the pole, along an integrity signal spectrum, i.e. 100% integrity, no deficiencies, to less than 5.0% integrity, full rotting, and all values in between. A second strike of the mallet, step 65 may be needed.

Figure 5B:
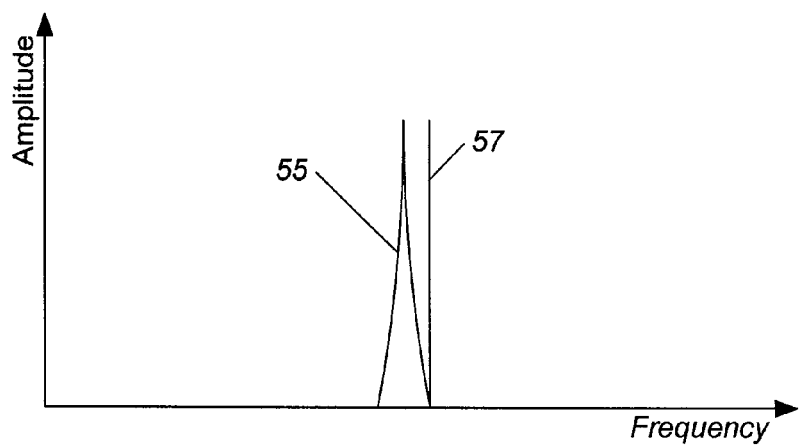
FIG. 5B illustrates the generated natural frequency of the test pole of FIG. 5A and the maximal natural frequency of a reference pole with the same geometrical parameters.
Figure 6B:
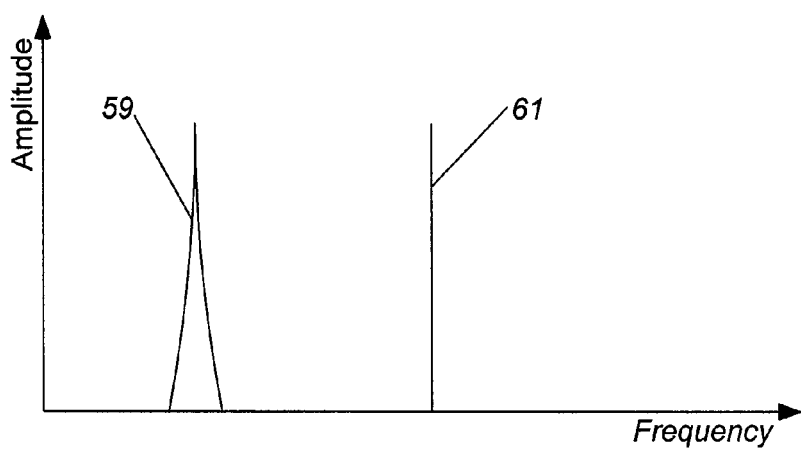
FIG. 6B illustrates the generated natural frequency of the test pole of FIG. 6A and the maximal natural frequency of a reference pole with the same geometrical parameters.

The data received and stored from the acoustic frequencies is filtered from noises and transformed from a time series to that of a frequency series and analysis to determine the acoustic model of the utility pole, step 60. The raw signal is converted from time-domain, see FIGS. 5A and 6A, into frequency-domain, see FIGS. 5B and 6B, in order to determine the value of the natural frequency of the tested pole. The natural frequency of the pole tested is to be compared with the maximal frequency of a pole with the same geometrical parameters. Referring to FIG. 5B, a curve 55 represents the generated natural frequency of the healthy test pole. Line 57 represents the maximal natural frequency of a reference pole with the same geometrical parameters. In FIG. 6B, a curve 59 represents the generated natural frequency of the rotten test pole. Line 61 represents the maximal natural frequency of a reference pole with the same geometrical parameters.

Once converted, the frequency series is analyzed in order to calculate the velocity of the propagation of sound waves and to extract the value of the natural frequency. These values will be used to define the actual acoustic model of the pole (see Equation. 4). Based on the analysis, other parameters or characteristics are determined, such as the value of the natural frequency, the reduction of the signal strength associated with transmission of the signal through a deteriorating and weakened utility pole, and/or the sonic wave speed value. The newly determined data is then compared to the mathematical data of step 52, see steps 66, 67, 68, and 70, and utility strength pole parameters, such as but not limited to residual resource/residual strength and the equivalent cross-section are estimated, step 72. The output data from step 72 can be stored internally within the memory of the pole integrity determining device 10, see step 74. Alternatively, the data can be stored utilizing radio frequency identification (RFID) technology, see step 76, which utilizes active, semi-active or passive RFID tags. The RFID tag, which is composed generally of a microchip, an antenna, and a power source such as a battery, are used to store the data. Other wireless technology, such as blue tooth technology, may be used to transfer and store all data, step 78. The data can be read, or transferred, to a reader which interprets the signal into usable data. A portable memory device, step 80 can be used to transfer the stored data within the pole integrity determining device 10 to one or more remotely located storage facilities or computers, see 68, and for further analysis and interpretation, step 70.

The comparison of two acoustic models (the ideal one with the actual one) enables estimation of the degradation of the pole under the influence of decay and external factors. The sound velocity will be used to estimate the actual bending stress of the pole. Based on this (sound velocity and degradation level) an actual model of the testing pole will be generated. This enables the calculation of the strength parameters of the pole (Equation 1). Along with these calculations, the integrity of the pole structure will be estimated (independently from other results) based on the sound attenuation. A low attenuation level indicates that the pole has an extensive deterioration or weak embodiment/attachment to the soil.

Based on all the data, determination of various indicators can be obtained, including: 1) residual/remaining strength (%), which shows in a percentage format the ratio of the pole actual strength (bending strength) to its maximal strength for the given wood species; 2) equivalent diameter/cross-section, which is an integral (average) value which shows the effective cross-section diameter (calculated for the ground line cross-section 35 cm below ground line) which provides the main bending strength of the pole and reflects the influence of any decays or external factors on the pole strength and stability; 3) ratio of the pole equivalent diameter to its external diameter, which expresses the degradation of the pole cross-section under the influence of decays and external factors, and shows the ratio of the equivalent diameter to the measured external (visual) one; and 4) rot indication which is an indicative value/sign which appears when the pole integrity is disrupted, such as a result of extensive deterioration or weak embodiment.

The present system and or device may further utilize a safety mode (steps 82-90). The safety mode allows for checking the safety of the utility pole and determining if the pole integrity has been disrupted prior to climbing. The device may include the necessary software to calculate the actual mechanical capacity of the pole, i.e. the breaking horizontal load applied to the pole tip, taking into account the presence of any decays and external static loads, such as any equipment, wires etc. Determination of such mode is based on the following calculation, using Equation (8)

$$F_{br} = \frac{M_{max} \cdot R(\%)}{H}; kgf$$

Where:
$F_{br}$=breaking horizontal load applied to the pole tip (pole capacity);
R=remaining strength in %;
$M_{max}$=maximum bending moment of a pole with same dimensions (height and diameter) made of healthy timber with maximum bending stress (495 kgf/cm$^2$);
H=Height of the pole (cm).

In addition to the actual capacity of the pole, the sum of additional loads (step 86), such as the lineman's weight, the ladder's weight, and wind load, can be calculated based on the following equation, Equation (9):

$$\Sigma P = P_{lm} + P_l + P_p + P_w; kgf$$

Where:
$P_{lm}$=weight of the lineman (constant value=125 kg);
$P_l$=weight of the ladder (constant value=30 kg);
$P_p$=weight of the pole (see Equation 10);
$P_w$=wind load (see Equation 11);
Where Equation 10 is $$P_p = \rho \cdot H \cdot \frac{\pi \cdot D^2}{4}; kg$$

Where:
D=pole's average diameter (taking into account the taper of the pole);
H=height of the pole (cm);
$\rho$=density of pine timber (constant value=520 kg/m$^3$).
Where Equation 11 is:

$$P_w = W \cdot \pi \cdot D \cdot H; kg$$

Where:
D=pole's average diameter (taking into account the taper of the pole);
H=height of the pole (cm);
W=wind pressure (kg/m$^2$) ranges from 0 to 200 and can be set by the user.

Although not required, it is preferable that two initial tests be passed before a determination of a safe pole can be determined. If the remaining strength of the pole is lower than 25% (crucial condition), the pole shall be considered unsafe. If the value is above 25%, the pole undergoes a second test. If the integrity of the pole is disrupted, then the pole shall be considered as unsafe, otherwise the following inequality shall be checked. The actual capacity of the pole ($F_{br}$) shall be compared with the sum of additional loads ($\Sigma P$) as following. If $F_{br} \geq 1.3 \cdot \Sigma P$, where 1.3 is a safety factor constant, then the pole is considered safe, otherwise the pole is unsafe.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A non-invasive method of determining the strength of an in service structure comprising the steps of:
    obtaining data related to an in service structure for which a determination as to its remaining strength is to be determined, said data to be obtained includes visual height of said in service structure, circumference of said in service structure, and material for which said in service structure is constructed;
    determining an acoustical model profile for said in service structure, said acoustic module profile determined by 1) striking said in service structure, whereby a vibrational frequency signal is generated, 2) detecting said vibrational frequency of said stricken in service structure, and 3) converting said vibration frequency of said stricken in service structure into an acoustic pattern;
    comparing said acoustic pattern of said in service structure to a reference acoustic pattern obtained from a standard structure having a predetermined integrity value to determine said remaining strength value of said in service structure, whereby said reference acoustic pattern has a predetermined structural integrity value for a structure having the same visual height, circumference, and material as that of said in service structure;
    determining a remaining strength value based on comparison of said in service structure acoustic pattern and said reference structure acoustic pattern, said remaining strength value represented as a quantitative assessment of useful life remaining for the entire in service structure expressed as a percentage, said percentage value representing the ratio of the actual pole strength to a maximal strength for an in service structure made of a particular material.

2. The non-invasive method of determining the strength of an in service structure according to claim 1 wherein said in service structure is made of wood.

3. The non-invasive method of determining the strength of an in service structure according to claim 1 wherein said wood structure is a utility pole.

4. The non-invasive method of determining the strength of an in service structure according to claim 1 wherein said in service structure is made of concrete.

5. The non-invasive method of determining the strength of an in service structure according to claim 1 wherein said acoustical model profile is determined using an acoustic sensor.

6. The non-invasive method of determining the strength of an in service structure according to claim 1 further including the steps of obtaining identification of said in service structure, the location of said in service structure, or combinations thereof.

7. The non-invasive method of determining the strength of an in service structure according to claim 1 wherein said step of determining a remaining strength value based on comparison of said in service structure acoustic pattern and said reference structure acoustic pattern uses one or more mathematical calculations.

8. The non-invasive method of determining the strength of an in service structure according to claim 1 further including a safety mode analysis.

9. The non-invasive method of determining the strength of an in service structure according to claim 1 wherein said standard value reference represents a structure having 100% integrity.

10. The non-invasive method of determining the strength of an in service structure according to claim 1 wherein said standard value reference represents a structure having less than 50% integrity.

11. The non-invasive method of determining the strength of an in service structure according to claim 1 wherein said standard value reference represents a structure having between 100% and 5% integrity.

12. The non-invasive method of determining the strength of an in service structure according to claim 1 wherein said calculation of said percentage further takes into account the presence of internal or external decay, the quality of anchoring to the ground, the quantity of moisture in said in service structure, static or dynamic loads associated with said in service structure, or combinations thereof.

13. The non-invasive method of determining the strength of an in service structure according to claim 1 further including a quantitative determination of equivalent diameter represented as an integral value of the effective cross-section diameter, a quantitative determination of a ratio of said pole equivalent diameter to its external diameter, a rot indication, or combinations thereof.

* * * * *